(12) United States Patent
Gonzalez et al.

(10) Patent No.: US 9,278,109 B2
(45) Date of Patent: Mar. 8, 2016

(54) COMPOSITIONS AND METHODS FOR THE PREVENTION OF CARDIOVASCULAR DISEASE

(71) Applicants: Michael J Gonzalez, Ponce, PR (US); Angel E Gil, Ponce, PR (US); Jesus G Gil, Coto Laurel, PR (US)

(72) Inventors: Michael J Gonzalez, Ponce, PR (US); Angel E Gil, Ponce, PR (US); Jesus G Gil, Coto Laurel, PR (US)

(*) Notice: Subject to any disclaimer, the term of this patent is extended or adjusted under 35 U.S.C. 154(b) by 0 days.

(21) Appl. No.: 14/017,864

(22) Filed: Sep. 4, 2013

(65) Prior Publication Data

US 2014/0017222 A1 Jan. 16, 2014

Related U.S. Application Data

(63) Continuation of application No. 13/657,074, filed on Oct. 22, 2012, now abandoned, and a continuation of application No. 13/388,570, filed on Dec. 28, 2011, now abandoned, and a continuation of application No. 12/177,193, filed on Jul. 22, 2008, now abandoned.

(51) Int. Cl.

| A01N 65/00 | (2009.01) |
|---|---|
| A61K 31/714 | (2006.01) |
| A61K 36/00 | (2006.01) |
| A23L 1/30 | (2006.01) |
| A23L 1/302 | (2006.01) |
| A23L 1/304 | (2006.01) |
| A23L 1/305 | (2006.01) |
| A61K 31/122 | (2006.01) |
| A61K 31/20 | (2006.01) |
| A61K 31/55 | (2006.01) |
| A61K 36/23 | (2006.01) |
| A61K 36/752 | (2006.01) |
| A61K 36/82 | (2006.01) |
| A61K 36/87 | (2006.01) |
| A61K 36/8962 | (2006.01) |
| A61K 45/06 | (2006.01) |
| A61K 31/185 | (2006.01) |
| A61K 31/198 | (2006.01) |
| A61K 31/202 | (2006.01) |
| A61K 31/205 | (2006.01) |
| A61K 31/355 | (2006.01) |
| A61K 31/375 | (2006.01) |
| A61K 31/385 | (2006.01) |
| A61K 31/4415 | (2006.01) |
| A61K 31/455 | (2006.01) |
| A61K 31/519 | (2006.01) |
| A61K 31/685 | (2006.01) |

(52) U.S. Cl.
CPC .............. *A61K 31/714* (2013.01); *A23L 1/30* (2013.01); *A23L 1/302* (2013.01); *A23L 1/3002* (2013.01); *A23L 1/304* (2013.01); *A23L 1/3006* (2013.01); *A23L 1/3008* (2013.01); *A23L 1/3045* (2013.01); *A23L 1/3051* (2013.01); *A61K 31/122* (2013.01); *A61K 31/185* (2013.01); *A61K 31/198* (2013.01); *A61K 31/20* (2013.01); *A61K 31/202* (2013.01); *A61K 31/205* (2013.01); *A61K 31/355* (2013.01); *A61K 31/375* (2013.01); *A61K 31/385* (2013.01); *A61K 31/4415* (2013.01); *A61K 31/455* (2013.01); *A61K 31/519* (2013.01); *A61K 31/55* (2013.01); *A61K 31/685* (2013.01); *A61K 36/00* (2013.01); *A61K 36/23* (2013.01); *A61K 36/752* (2013.01); *A61K 36/82* (2013.01); *A61K 36/87* (2013.01); *A61K 36/8962* (2013.01); *A61K 45/06* (2013.01)

(58) Field of Classification Search
CPC ......................................................... A61K 36/00
USPC ........................................................... 424/725
See application file for complete search history.

(56) References Cited

U.S. PATENT DOCUMENTS

| 4,374,082 A | 2/1983 | Hochschild |
|---|---|---|
| 5,215,754 A | 6/1993 | Valorose et al. |
| 5,965,162 A | 10/1999 | Fuisz et al. |
| 6,495,177 B1 | 12/2002 | De Vries et al. |
| 6,800,292 B1 | 10/2004 | Murad |
| 2001/0031744 A1 | 10/2001 | Kosbab |
| 2005/0249803 A1 | 11/2005 | Udell |
| 2007/0116799 A1 | 5/2007 | Lahrsow |

OTHER PUBLICATIONS

Thom et al., 113 Circulation e85-e151 (2006).
Sarter, 16(4) J. Cardiovasc. Nurs. 9-20 (2002).
Singh et al., 65 Nutr. Rev. 286-93 (2007).
Belardinelli et al., 27(22) Eur. Heart J. 2675-81 (2006).
Middleton Jr., et al., 52(4) Pharm. Rev. 673-751 (2000).
Bagchi et al., 523-524 Mutat. Res. 87-97 (2003).
Pryor, 28(1) Free Radic. Biol. Med. 141-64 (2000).
Dutta et al., 22(4) J. Am. Coll. Nutr. 258-68 (2003).
Parker et al., 268(15) J. Biol. Chem. 11230-38 (1993).
Kris-Etherton, 106 Circulation 2747-57 (2002).

(Continued)

*Primary Examiner* — Michael Meller
(74) *Attorney, Agent, or Firm* — Don J. Pelto; Sheppard Mullin Richter & Hampton LLP

(57) ABSTRACT

The present invention relates to compositions comprising vitamins, minerals and other nutrients and methods for using these compositions for nutritional supplementation to prevent and/or alleviate a patient from the occurrence or negative effects of cardiovascular disease. Specifically, the invention relates to compositions and methods of administering compositions comprising natural $CoQ_{10}$, natural Omega-3 fatty acids, natural bioflavonoids, natural vitamin E, amino acids and derivatives thereof, minerals, extra virgin olive oil, lecithin, B-complex vitamins, and antioxidants.

1 Claim, No Drawings

(56) References Cited

OTHER PUBLICATIONS

Von Schacky C, 2(3) Vasc. Health Risk Manag. 251-62 (2006).
Schlaich, 153(2) Atheroscler 383-89 (2000).
Hanratty, 85(3) Heart 326-30 (2001).
Verhoef et al., 143(9) Am J. Epidemiol 845-59 (1996).
Das, 19(7-8) Nutr. 686-92 (2003).
Rebouche, 6 The FASEB Journal, 3379-86 (1992).
Ferrari et al., 1033 Ann. N.Y. Acad. Sci. 79-91 (2004).
Hagen et al., 99(4) PNAS 1870-75 (2002).
Olthof et al., 133 J. Nutr. 4135-38 (2003).
Wollin et al., 133(11) J. of Nutr. 3327-30 (2003).
Anderson et al., 70(3) Am. J. Clin. Nutr. 307-08 (1999).
Shechter et al. 102(19) Circulation 2353-58 (2000).
Rayman, 356(9225) Lancet. 233-41 (2000).
Wei et al., 79(1) Am. J. Clin. Nutr., 80-5 (2004).
Lockitch et al. 52(3) Am. J. Clin. Nutr. 572 (1990).
Psaltopoulou et al., 80(4) Am. J. Clin Nutr. 1012-1018 (2004).
Messina et al., 98(18) J. Natl. Cancer Inst. 1275-84 (2006).
National Research Council, Recommended Dietary Allowances 10th ed., 159-60 (1989).
2002 http://www.natureslife.com/PPS/FSMulti.pdf.
2011 http://www.womentowomen.com/heartdiseaseandstroke/cardiovasculardiseases.aspx.
2011 http://www.americanheart.org/presenter.jhtml?identifier-4565.

COMPOSITIONS AND METHODS FOR THE PREVENTION OF CARDIOVASCULAR DISEASE

CROSS REFERENCE TO RELATED APPLICATION

This application is a continuation and claims the benefit under 35 U.S.C. §120 of U.S. patent application Ser. No. 13/657,074, filed Oct. 22, 2012, now abandoned, which is a continuation of and claims the benefit under 35 U.S.C. §120 of U.S. patent application Ser. No. 13/338,570, filed Dec. 28, 2011, no abandoned, which is a continuation of U.S. patent application Ser. No. 12/177,193, filed Jul. 22, 2008, now abandoned, which is expressly incorporated fully herein by reference.

FIELD OF THE INVENTION

The present invention relates to compositions comprising vitamins, minerals and other nutrients and methods for using these compositions for nutritional supplementation to prevent and/or alleviate a patient from the occurrence or negative effects of cardiovascular disease.

BACKGROUND OF THE INVENTION

Cardiovascular disease is the number one cause of death of both men and women in the United States. Thom et al., 113 CIRCULATION e85-e151 (2006). Nearly 2,500 Americans die of cardiovascular disease each day, an average of one death every thirty-five seconds. Id. Although there are many risk factors related to cardiovascular disease, vitamin and nutrient deficiency due to poor intake of nutrients or vitamins remains one of the most prevalent risk factors. The nutrients that assist in such prevention, however, come from a wide variety of food groups such as fruits, vegetables and fish. Id. Although certain patients may consume certain nutritious foods, it is less likely that a patient will consume a balanced diet that includes the wide range of beneficial nutrients that reduce the risk of cardiovascular disease. To assist in this problem, it would therefore be beneficial to have a nutritional supplement that includes essential vitamins or nutrients from various food groups that assist in the prevention and/or alleviation of cardiovascular disease.

Research has shown that nutritional supplementation may play a vital role in protecting a patient from the occurrence or negative effects of cardiovascular disease. Specifically, it is believed that coenzyme $Q_{10}$, omega-3 polyunsaturated fatty acids, bioflavonoids, vitamin E, amino acids or derivatives thereof, minerals, B-complex vitamins, and other antioxidants or ingredients may assist through their various physiological roles to prevent and/or alleviate the occurrence or negative effects of cardiovascular disease.

SUMMARY OF THE INVENTION

The present invention provides compositions and methods of using these compositions for both prophylactic and therapeutic nutritional supplementation. Specifically, the present invention includes vitamins and minerals that prevent and/or alleviate the occurrence or negative effects of cardiovascular diseases. The present invention also may be formulated to exclude vitamins, nutrients and minerals known to inhibit the beneficial effects of the included vitamins and minerals. The compositions of the present invention may be in a swallowable, chewable or dissolvable form according to an individual patient's preference. Choice in dosage form promotes ease of administration and compliance with dosing regimens.

In one embodiment of the present invention, the compositions may comprise natural $CoQ_{10}$, natural omega-3 fatty acids, natural bioflavonoids, natural vitamin E, amino acids and derivatives thereof, minerals, extra virgin olive oil, lecithin, B-complex vitamins, and antioxidants.

In another embodiment, the compositions of the present invention may comprise B-complex vitamins selected from one or more of the group consisting of vitamin $B_1$, vitamin $B_2$, vitamin $B_3$, vitamin $B_5$, vitamin $B_6$, vitamin $B_7$, vitamin $B_9$ and vitamin $B_{12}$.

In another embodiment, the compositions of the present invention may comprise vitamin $B_3$ in the forms of nicotinic acid and niacinamide ascorbate.

In another embodiment, the compositions of the present invention may comprise vitamin $B_6$ in the form of pyridoxine.

In another embodiment, the compositions of the present invention may comprise vitamin $B_9$ in the form of folic acid.

In another embodiment, the compositions of the present invention may comprise vitamin $B_{12}$ in the form of cyanocobalamin.

In another embodiment, the compositions of the present invention may comprise natural omega-3 fatty acids selected from one or more of the group consisting of eicosapentaenoic acid (EPA), docosahexaenoic acid (DHA), α-linolenic acid, stearidonic acid, eicosatetraenoic acid, docosapentaenoic acid, octadecatrienoic acid and octadecatetraenoic acid.

In another embodiment of the present invention, natural bioflavonoids may be extracted from a natural source selected from one or more of the group consisting of grape seeds, onions, parsley, legumes, green tea, and citrus fruits. In another embodiment of the present invention, natural bioflavonoids may comprise grape seed extract.

In another embodiment, the compositions of the present invention may comprise bioflavonoids selected from one or more of the group consisting of oligomeric proanthocyanidins (OPC's), epicatechin, genistein, hesperidin, quercetin, rutin, narirutin, naringin, hesperetin, neohesperidin, tangeretin, nobiletin and sinensetin.

In another embodiment, the compositions of the present invention may comprise chelated minerals wherein the metal is selected from one or more of the group consisting of magnesium, zinc, calcium, phosphorous, copper, manganese, chromium, selenium, sodium, potassium, chloride, and iron.

In another embodiment, the compositions of the present invention may comprise magnesium chelated to an amino acid. In another embodiment, the compositions of the present invention may comprise L-Seleno-Methionine.

In another embodiment, the compositions of the present invention may comprise vitamin E selected from one or more of the group consisting of natural tocopherols and natural tocotrienols.

In another embodiment, the compositions of the present invention may comprise natural mixed tocopherols selected from one or more of the group consisting of gamma tocopherol, delta tocopherol, alpha tocopherol and beta tocopherol.

In another embodiment, the compositions of the present invention may comprise natural mixed tocotrienols selected from one or more of the group consisting of gamma tocotrienol, delta tocotrienol and alpha tocotrienol.

In another embodiment, the compositions of the present invention may comprise amino acids selected from one or more of the group consisting of proline, phenylalanine, methionine, threonine, tryptophan, histidine, isoleucine, leucine, asparagine, aspartic acid, glutamic acid, glutamine, serine, tyrosine, valine, lysine, alanine, glycine, tryptophan, cysteine, TMG (trimethyl glycine/Betaine), L taurine, L-carnitine, acetyl-L-carnitine, N,N-dimethyl glycine and N-acetylcysteine.

In another embodiment, the compositions of the present invention may comprise antioxidants selected from one or more of the group consisting of vitamin C (ascorbic acid), alpha-lipoic acid, ascorbyl palmitate, butylated hydroxyanisole, butylated hydroxytoluene, hypophosphorous acid, monothioglycerol, propyl gallate, sodium ascorbate, sodium bisulfite, sodium formaldehyde sulfoxylate, sodium metabisulfite, pycnogenol, superoxide dismutase, pine bark grape seed complex, garlic, carotenoids, choline, metabisulfite, catechin, glangin, rutin, luteolin, morin, fisetin, silymerin, ascorbyl palmitate, apigenin, gingkolides, hesperitin, cyanidin, citrin sodium bisulfite or mixtures thereof.

In another embodiment, the compositions of the present invention may include vitamin C in the form of calcium ascorbate.

In another embodiment of the present invention, the compositions may be substantially free of other added vitamins, nutrients and minerals. The other added nutrient may be another omega-3 fatty acid selected from one or more of the group consisting of α-linolenic acid, stearidonic acid, eicosatetraenoic acid, docosapentaenoic acid, octadecatrienoic acid and octadecatetraenoic acid. The other added nutrient may be another natural biofavonoid selected from one or more of the group consisting of epicatechin, genistein, hesperidin, quercetin, rutin, narirutin, naringin, hesperetin, neohesperidin, tangeretin, nobiletin and sinensetin. The other added mineral may be another metal selected from one of more of the group consisting of zinc, calcium, phosphorous, copper, manganese, chromium, sodium, potassium, chloride, and iron. The other added nutrient may be another amino acid selected from one or more of the group consisting of proline, phenylalanine, threonine, tryptophan, histidine, isoleucine, leucine, asparagine, aspartic acid, glutamic acid, glutamine, serine, tyrosine, valine, lysine, alanine, glycine, tryptophan, cysteine, N,N-dimethyl glycine and N-acetylcysteine. The other added nutrient may be another antioxidant selected from one or more of the group consisting of ascorbyl palmitate, butylated hydroxyanisole, butylated hydroxytoluene, hypophosphorous acid, monothioglycerol, propyl gallate, sodium ascorbate, sodium bisulfite, sodium formaldehyde sulfoxylate, sodium metabisulfite, pycnogenol, superoxide dismutase, pine bark grape seed complex, garlic, carotenoids, choline, metabisulfite, catechin, glangin, rutin, luteolin, morin, fisetin, silymerin, ascorbyl palmitate, apigenin, gingkolides, hesperitin, cyanidin, citrin and sodium bisulfite.

In another embodiment, the compositions of the present invention may comprise pharmaceutically acceptable carriers, such as one or more of binders, diluents, lubricants, glidants, colorants, emulsifiers, disintegrants, starches, water, oils, alcohols, preservatives, and sugars.

In another embodiment of the present invention, the compositions may comprise omega-3 fatty acids such as natural DHA omega-3 and natural EPA omega-3, bioflavonoids such as natural grape seed extract bioflavonoids or OPC's, vitamin E such as natural mixed tocotrienols, natural alpha tocotrienol, natural delta tocotrienol, natural gamma tocotrienol, natural mixed tocopherols, natural beta tocopherol, natural alpha tocopherol, natural delta tocopherol and natural gamma tocopherol, amino acids and derivatives thereof such as L-taurine, TMG (trimethyl glycine/Betaine), L-carnitine, and acetyl-L-carnitine, minerals such as magnesium and L-Seleno-Methionine, B-complex vitamins such as cyanocobalamin, pyridoxine, niacinamide ascorbate, nicotinic acid, and folic acid, and antioxidants such as Vitamin C (calcium ascorbate) and alpha-lipoic acid.

In another embodiment of the present invention, the compositions may comprise about 75 mg to about 25 mg lecithin; about 112.5 mg to about 322.5 mg extra virgin olive oil; about 12.5 mg to about 37.5 mg L-taurine; about 25 mg to about 75 mg TMG; about 25 mg to about 75 mg L-carnitine; about 6.25 mg to about 18.75 mg acetyl-L-carnitine; about 25 mcg to about 75 mcg L-Seleno-Methionine; about 50 mg to about 150 mg magnesium chelated to an amino acid; about 25 mcg to about 75 mcg cyanocobalamin; about 12.5 mg to about 37.5 mg pyridoxine; about 6.25 mg to about 18.75 mg niacinamide ascorbate; about 6.25 mg to about 18.75 mg nicotinic acid; about 0.25 mg to about 0.75 mg folic acid; about 30 mg to about 90 mg DHA omega-3; about 45 mg to about 135 mg EPA omega-3; about 125 mg to about 375 mg calcium ascorbate; about 12.5 mg to about 37.5 mg alpha-lipoic acid; about 25 mg to about 75 mg grape seed extract bioflavonoids or OPCs; about 18.75 mcg to about 56.25 mcg alpha tocotrienol; about 31.25 mcg to about 93.75 mcg delta tocotrienol; about 275 mcg to about 825 mcg gamma tocotrienol; a total of about 6.25 mg to about 18.75 mg mixed tocotrienols; about 0.75 IU to about 2.25 IU beta tocopherol; about 7.5 IU to about 22.5 IU alpha tocopherol; about 12 IU to about 36 IU delta tocopherol; about 45 IU to about 135 IU gamma tocopherol; a total of about 75 IU to about 225 IU of mixed tocopherols; and about 15 mg to about 45 mg $CoQ_{10}$.

In another embodiment of the present invention, the compositions may comprise 50 mg lecithin; about 215 mg extra virgin olive oil; about 25 mg L-taurine; about 50 mg TMG; about 50 mg L-carnitine; about 12.5 mg acetyl-L-carnitine; about 50 mcg L-Seleno-Methionine; about 100 mg magnesium chelated to an amino acid; about 50 mcg cyanocobalamin; about 25 mg pyridoxine; about 12.5 mg niacinamide ascorbate; about 12.5 mg icotinic acid; about 0.5 mg folic acid; about 60 mg DHA omega-3; about 90 mg EPA omega-3; about 250 mg calcium ascorbate; about 25 mg alpha-lipoic acid; about 50 mg grape seed extract bioflavonoids or OPCs; about 37.5 mcg alpha tocotrienol; about 62.5 mcg delta tocotrienol; about 550 mcg gamma tocotrienol; about a total of 12.5 mg mixed tocotrienols; about 1.5 IU beta tocopherol; about 15 IU alpha tocopherol; about 24 IU delta tocopherol; about 90 IU gamma tocopherol; about a total of 150 IU of mixed tocopherols; and about 30 mg $CoQ_{10}$.

In another embodiment of the present invention, the compositions may be administered to a patient.

In another embodiment of the present invention, the compositions may be administered to a patient orally.

In another embodiment of the present invention, the compositions may be in the dosage form of a softgel.

In another embodiment of the present invention, the compositions may be administered to a patient to prevent and/or alleviate the occurrence or negative effects of cardiovascular disease.

In one embodiment of the present invention, the methods may utilize compositions comprising natural $CoQ_{10}$, natural omega-3 fatty acids, natural bioflavonoids, natural vitamin E, amino acids or derivatives thereof, minerals, extra virgin olive oil, lecithin, B-complex vitamins, and antioxidants.

In one embodiment of the present invention, the methods may utilize compositions comprising B-complex vitamins in one or more of the vitamins selected from the group consisting of vitamin $B_1$, vitamin $B_2$, vitamin $B_3$, vitamin $B_5$, vitamin $B_6$, vitamin $B_7$, vitamin $B_9$ and vitamin $B_{12}$.

In another embodiment of the present invention, the methods may utilize compositions comprising vitamin $B_3$ in the form of nicotinic acid and niacinamide ascorbate.

In another embodiment of the present invention, the methods may utilize compositions comprising vitamin $B_6$ in the form of pyridoxine.

In another embodiment of the present invention, the methods may utilize compositions comprising vitamin $B_9$ in the form of folic acid.

In another embodiment of the present invention, the methods may utilize compositions comprising vitamin $B_{12}$ in the form of cyanocobalamin.

In another embodiment of the present invention, the methods may utilize compositions comprising omega-3 fatty acids selected from one or more of the group consisting of eicosapentaenoic acid, docosahexaenoic acid, α-linolenic acid, stearidonic acid, eicosatetraenoic acid, docosapentaenoic acid, octadecatrienoic acid and octadecatetraenoic acid.

In another embodiment of the present invention, the methods may utilize compositions comprising bioflavonoids extracted from a natural source selected from one or more of the group consisting of grape seeds, onions, parsley, legumes, green tea, and citrus fruits.

In another embodiment of the present invention, the methods may utilize compositions comprising bioflavonoids selected from one or more of the group consisting of oligomeric proanthocyanidins (OPC's), epicatechin, genistein, hesperidin, quercetin, rutin, narirutin, naringin, hesperetin, neohesperidin, tangeretin, nobiletin and sinensetin.

In another embodiment of the present invention, the methods may utilize compositions comprising chelated minerals selected from one or more of the group consisting of magnesium, zinc, calcium, phosphorous, copper, manganese, chromium, selenium, sodium, potassium, chloride, and iron.

In another embodiment of the present invention, the methods may utilize compositions comprising magnesium chelated to an amino acid. In another embodiment of the present invention, the methods may utilize compositions comprising L-Seleno-Methionine.

In another embodiment of the present invention, the methods may utilize compositions comprising vitamin E selected from one or more of the group consisting of natural tocopherols and natural tocotrienols.

In another embodiment of the present invention, the methods may utilize compositions comprising natural mixed tocopherols selected from one or more of the group consisting of gamma tocopherol, delta tocopherol, alpha tocopherol and beta tocopherol.

In another embodiment of the present invention, the methods may utilize compositions comprising natural mixed tocotrienols selected from one or more of the group consisting of gamma tocotrienol, delta tocotrienol and alpha tocotrienol.

In another embodiment of the present invention, the methods may utilize compositions comprising amino acids selected from one or more of the group consisting of proline, phenylalanine, methionine, threonine, tryptophan, histidine, isoleucine, leucine, asparagine, aspartic acid, glutamic acid, glutamine, serine, tyrosine, valine, lysine, alanine, glycine, tryptophan, cysteine, TMG (trimethyl glycine/Betaine), L taurine, L-carnitine, acetyl-L-carnitine, N,N-dimethyl glycine and N-acetylcysteine.

In another embodiment of the present invention, the methods may utilize compositions comprising other antioxidants selected from one or more of the group consisting of vitamin C (ascorbic acid), alpha-lipoic acid, ascorbyl palmitate, butylated hydroxyanisole, butylated hydroxytoluene, hypophosphorous acid, monothioglycerol, propyl gallate, sodium ascorbate, sodium bisulfite, sodium formaldehyde sulfoxylate, sodium metabisulfite, pycnogenol, superoxide dismutase, pine bark grape seed complex, garlic, carotenoids, choline, metabisulfite, catechin, glangin, rutin, luteolin, morin, fisetin, silymerin, ascorbyl palmitate, apigenin, gingkolides, hesperitin, cyanidin, citrin sodium bisulfite or mixtures thereof.

In another embodiment of the present invention, the methods may utilize compositions comprising vitamin C in the form of calcium ascorbate.

In another embodiment of the present invention, the methods may utilize compositions substantially free of other added vitamins nutrients and minerals. The other added nutrient may be another omega-3 fatty acid selected from one or more of the group consisting of α-linolenic acid, stearidonic acid, eicosatetraenoic acid, docosapentaenoic acid, octadecatrienoic acid and octadecatetraenoic acid. The other added nutrient may be another natural biofavonoid selected from one or more of the group consisting of epicatechin, genistein, hesperidin, quercetin, rutin, narirutin, naringin, hesperetin, neohesperidin, tangeretin, nobiletin and sinensetin. The other added mineral may be another metal selected from one of more of the group consisting of zinc, calcium, phosphorous, copper, manganese, chromium, sodium, potassium, chloride, and iron. The other added nutrient may be another amino acid selected from one or more of the group consisting of proline, phenylalanine, threonine, tryptophan, histidine, isoleucine, leucine, asparagine, aspartic acid, glutamic acid, glutamine, serine, tyrosine, valine, lysine, alanine, glycine, tryptophan, cysteine, N,N-dimethyl glycine and N-acetylcysteine. The other added nutrient may be another antioxidant selected from one or more of the group consisting of ascorbyl palmitate, butylated hydroxyanisole, butylated hydroxytoluene, hypophosphorous acid, monothioglycerol, propyl gallate, sodium ascorbate, sodium bisulfite, sodium formaldehyde sulfoxylate, sodium metabisulfite, pycnogenol, superoxide dismutase, pine bark grape seed complex, garlic, carotenoids, choline, metabisulfite, catechin, glangin, rutin, luteolin, morin, fisetin, silymerin, ascorbyl palmitate, apigenin, gingkolides, hesperitin, cyanidin, citrin and sodium bisulfite.

In another embodiment of the present invention, the methods may utilize compositions comprising pharmaceutically acceptable carriers, such as one or more of binders, diluents, lubricants, glidants, colorants, emulsifiers, disintegrants, starches, water, oils, alcohols, preservatives, and sugars.

In another embodiment of the present invention, the methods may utilize compositions comprising omega-3 fatty acids such as natural DHA omega-3 and natural EPA omega-3, bioflavonoids such as natural grape seed extract bioflavonoids or OPC's, vitamin E such as natural mixed tocotrienols, natural alpha tocotrienol, natural delta tocotrienol, natural gamma tocotrienol, natural mixed tocopherols, natural beta tocopherol, natural alpha tocopherol, natural delta tocopherol and natural gamma tocopherol, amino acids and derivatives thereof such as L-taurine, TMG (trimethyl glycine/Betaine), L-carnitine, and acetyl-L-carnitine, minerals such as magnesium and L-Seleno-Methionine, B-complex vitamins such as cyanocobalamin, pyridoxine, niacinamide ascorbate, nicotinic acid, and folic acid, and antioxidants such as Vitamin C (calcium ascorbate) and alpha-lipoic acid.

In another embodiment of the present invention, the methods may utilize compositions comprising about 75 mg to about 25 mg lecithin; about 112.5 mg to about 322.5 mg extra virgin olive oil; about 12.5 mg to about 37.5 mg L-taurine; about 25 mg to about 75 mg TMG; about 25 mg to about 75 mg L-carnitine; about 6.25 mg to about 18.75 mg acetyl-L- carnitine; about 25 mcg to about 75 mcg L-Seleno-Methionine; about 50 mg to about 150 mg magnesium chelated to an amino acid; about 25 mcg to about 75 mcg cyanocobalamin; about 12.5 mg to about 37.5 mg pyridoxine; about 6.25 mg to about 18.75 mg niacinamide ascorbate; about 6.25 mg to about 18.75 mg nicotinic acid; about 0.25 mg to about 0.75 mg folic acid; about 30 mg to about 90 mg DHA omega-3; about 45 mg to about 135 mg EPA omega-3; about 125 mg to about 375 mg calcium ascorbate; about 12.5 mg to about 37.5 mg alpha-lipoic acid; about 25 mg to about 75 mg grape seed extract bioflavonoids or OPCs; about 18.75 mcg to about 56.25 mcg alpha tocotrienol; about 31.25 mcg to about 93.75 mcg delta tocotrienol; about 275 mcg to about 825 mcg gamma tocotrienol; a total of about 6.25 mg to about 18.75 mg mixed tocotrienols; about 0.75 IU to about 2.25 IU beta tocopherol; about 7.5 IU to about 22.5 IU alpha tocopherol; about 12 IU to about 36 IU delta tocopherol; about 45 IU to about 135 IU gamma tocopherol; a total of about 75 IU to about 225 IU mixed tocopherols; and about 15 mg to about 45 mg $CoQ_{10}$.

In another embodiment of the present invention, the methods may utilize compositions comprising 50 mg lecithin; about 215 mg extra virgin olive oil; about 25 mg L-taurine; about 50 mg TMG; about 50 mg L-carnitine; about 12.5 mg acetyl-L-carnitine; about 50 mcg L-Seleno-Methionine; about 100 mg magnesium chelated to an amino acid; about 50 mcg cyanocobalamin; about 25 mg pyridoxine; about 12.5 mg niacinamide ascorbate; about 12.5 mg nicotinic acid; about 0.5 mg folic acid; about 60 mg DHA omega-3; about 90 mg EPA omega-3; about 250 mg calcium ascorbate; about 25 mg alpha-lipoic acid; about 50 mg grape seed extract bioflavonoids or OPCs; about 37.5 mcg alpha tocotrienol; about 62.5 mcg delta tocotrienol; about 550 mcg gamma tocotrienol; about a total of 12.5 mg mixed tocotrienols; about 1.5 IU beta tocopherol; about 15 IU alpha tocopherol; about 24 IU delta tocopherol; about 90 IU gamma tocopherol; about a total of 150 IU of mixed tocopherols; and about 30 mg $CoQ_{10}$.

In another embodiment of the present invention, the methods may utilize compositions that may be administered to a patient.

In another embodiment of the present invention, the methods may utilize compositions that may be administered to a patient orally.

In another embodiment of the present invention, the methods may utilize compositions in the form of a softgel.

In another embodiment of the present invention, the methods may utilize compositions that may be administered to a patient to prevent and/or alleviate the occurrence or negative effects of cardiovascular disease.

In another embodiment of the present invention, the methods may utilize compositions that may be administered to a patient once a day. In a further embodiment of the present invention, the methods may utilize compositions that may be administered to a patient twice a day.

DETAILED DESCRIPTION OF THE INVENTION

It is understood that the present invention is not limited to the particular methodologies, protocols, fillers, excipients, etc., described herein, as these may vary. It is also to be understood that the terminology used herein is used for the purpose of describing particular embodiments only, and is not intended to limit the scope of the present invention. It must be noted that as used herein and in the appended claims, the singular forms "a," "an," and "the" include the plural reference unless the context clearly dictates otherwise. Thus, for example, a reference to "a vitamin" is a reference to one or more vitamins and includes equivalents thereof known to those skilled in the art and so forth.

Unless defined otherwise, all technical and scientific terms used herein have the same meanings as commonly understood by one of ordinary skill in the art to which this invention belongs. Specific methods, devices, and materials are described, although any methods and materials similar or equivalent to those described herein can be used in the practice or testing of the present invention.

The term "subject," as used herein, comprises any and all organisms and includes the term "patient." "Subject" may refer to a human or any other animal.

The phrase "pharmaceutically acceptable," as used herein, refers to those compounds, materials, compositions and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "swallowable form" refers to any compositions that do not readily dissolve when placed in the mouth and may be swallowed whole without any chewing or discomfort. Such compositions, in one embodiment, may have a shape containing no sharp edges and a smooth, uniform and substantially bubble free outer coating.

The term "dosage form," as used herein, is the form in which the dose is to be administered to the subject or patient. The drug or supplement is generally administered as part of a formulation that includes nonmedical agents. The dosage form has unique physical and pharmaceutical characteristics. Dosage forms may be solid, liquid or gaseous. Solid forms include, but are not limited to pills, capsules, tablets, gel caplets, softgels, lozenges, wafers etc.

The term "substantially free of added" as used herein, means free from therapeutically effective amounts of compounds when administered in suggested doses, but may include trace amounts of compounds in non-therapeutically effective amounts.

As used herein, the terms "inactive," "inert," "excipient," and/or "formulatory" refer to any compound that is an inactive ingredient of a described composition. The definition of "inactive ingredient" as used herein follows that of the U.S. Food and Drug Administration, as defined in 21 C.F.R. 201.3 (b)(8), which is any component of a drug product other than the active ingredient. By "active ingredient," then, is meant any compound intended to furnish pharmacological activity or other direct effect in the diagnosis, cure, mitigation, treatment and/or prevention of a condition. See 21 C.F.R. 210.3 (b)(7). Further, "active ingredients" include those compounds of the composition that may undergo chemical change during the manufacture of the composition and be present in the final composition in a modified form intended to furnish an activity or effect. Id.

The term "natural" as used herein, means any compound or form of matter that exists in or is derived from plants, animals, and/or other microorganisms as opposed to compounds or forms of matter that are artificial, synthetic and/or made by chemical synthesis Cardiovascular disease is the number one cause of death of both men and women in the United States. Thom et al., 113 CIRCULATION e85-e151 (2006). Nearly 2,500 Americans die of cardiovascular disease each day, an average of one death every thirty-five seconds. Id. Although there are many risk factors related to cardiovascular disease, vitamin and nutrient deficiency due to poor intake of nutrients or vitamins remains one of the most prevalent risk factors. The nutrients that assist in cardiovascular disease prevention, however, come from a wide variety of food groups such as fruits, vegetables and fish. Id. Although certain patients may consume certain nutritious foods, it is less likely that a patient will consume a balanced diet that includes the wide range of beneficial nutrients that reduce the risk of cardiovascular disease. To assist in this problem, it would therefore be beneficial to have a nutritional supplement that includes essential vitamins, minerals or nutrients from various food groups that aid in the prevention and/or alleviation of cardiovascular disease.

Therefore, the compositions and methods of the present invention provide a nutritional supplement to prevent, and/or alleviate the occurrence or negative effects of cardiovascular disease. The compositions and methods of the present invention may be administered to or directed to a subject such as a human or any other organism. Specifically, the compositions and methods of the present invention may include natural vitamins, nutrients or minerals, and including, but not limited to, natural Coenzyme $Q_{10}$, natural Omega-3 polyunsaturated fatty acids, natural bioflavonoids, vitamin E, amino acids or derivatives thereof, minerals, B-complex vitamins, extra virgin olive oil, lecithin, and other beneficial antioxidants. In a specific embodiment, vitamins and or nutrients that inhibit these compounds' beneficial effects may be substantially free from the compositions and methods of the present invention.

Coenzyme $Q_{10}$ ($CoQ_{10}$) is an important natural antioxidant and an essential component of the mitochondrial respiratory chain and therefore, the generation of ATP. $CoQ_{10}$ is biosynthesised in the body and shares a common synthetic pathway with cholesterol. Sarter, 16(4) J. CARDIOVASC. NURS. 9-20 (2002). There is evidence to support the therapeutic value of $CoQ_{10}$ as an adjunct to standard medical therapy in cardiovascular disease. Singh et al., 65 NUTR. REV. 286-93 (2007). It is believed that $CoQ_{10}$ asserts its beneficial effects by both being an antioxidant and due to its bioenergetic effect. It has been observed that $CoQ_{10}$ levels are decreased in severe cardiocirulatory dysfunction as well as in conditions of high oxidative stress. Belardinelli et al., 27(22) EUR. HEART J. 2675-81 (2006). In fact, administration of $CoQ_{10}$ to patients with cardiovascular disease has shown to specifically improve myocardial metabolic function, reduce blood pressure, and reduce myocardial thickness. Sarter et al.

In one embodiment, the compositions and methods of the present invention may include natural $CoQ_{10}$ in amounts ranging from about 15 mg to about 45 mg. In another embodiment, natural $CoQ_{10}$ may be included in an amount of about 30 mg. In another specific embodiment, the compositions and methods of the present invention may consist of natural $CoQ_{10}$.

Bioflavonoids, also known as flavonoids, include the subgroups flavonols, flavones, isoflavones, flavanones, catechins, and anthocyanidins. Bioflavonoids have antioxidant properties, are nearly ubiquitous in plants and are recognized as the pigments responsible for the colors of leaves, especially in autumn. They are rich in natural plants and foods such as seeds, citrus fruits, olive oil, tea, and red wine. Bioflavonoids appear to be beneficial against heart disease by protecting LDL against oxidation, which may reduce the risk of heart attacks. Middleton, Jr., et al., 52(4) PHARM. REV. 673-751 (2000).

A particularly potent bioflavonoid, oligomeric proanthocyanidins (OPC's), are thought to be potent antioxidants possessing 20 times the antioxidant power of vitamin C and 50 times the antioxidant power of vitamin E. These antioxidants have been individually used both topically and orally to protect the skin from various afflictions. See, for example, U.S. Pat. No. 6,800,292 which is expressly incorporated by reference herein.

Grape seed extract, which is rich in OPC's, is also thought to be particularly effective against cardiovascular disease. Specifically, research suggests that grape seed proanthocyanidin extract supplementation improves cardiac functional assessment including post-ischemic left ventricular function, reduced myocardial infarct size, reduced ventricular fibrillation (VF) and decreased the amount of reactive oxygen species (ROS) in subjects. Bagchi et al., 523-524 MUTAT. RES. 87-97 (2003).

In a specific embodiment, the compositions and methods of the present invention may include bioflavonoids. In a specific embodiment, the compositions and methods may include bioflavonoids, extracted from a natural source selected from one or more of plants or foods consisting of grape seeds, onions, parsley, legumes, green tea, and citrus fruits. In a specific embodiment, the compositions and methods of the present invention may include natural grape seed extract bioflavanoids. In another specific embodiment, the compositions and methods may include bioflavonoids selected from one or more of the group consisting of oligomeric proanthocyanidins (also known as procyanidolic oligomers), epicatechin, genistein, hesperidin, quercetin, rutin, narirutin, naringin, hesperetin, neohesperidin, tangeretin, nobiletin and sinensetin. In another specific embodiment, the compositions and methods may include bioflavonoids extracted from natural grape seeds that comprise oligomeric proanthocyanidins (OPC's).

In another specific embodiment, the compositions and methods may include grape seed extract bioflavonoids or OPC's in the range of about 25 mg to about 75 mg. In another specific embodiment, the compositions and methods may include grape seed extract bioflavonoids or OPC's in the amount of about 50 mg.

Vitamin E is a fat-soluble antioxidant found in biological membranes where it protects the phospholipid membrane from oxidative stress. Vitamin E is available in abundance in common nuts and seeds such as almonds, peanuts, sunflower seeds, filbert and vegetable oils. Vitamin E is thought to assist in the prevention of cardiovascular disease by inhibiting the oxidation of unsaturated lipids in the low-density lipoprotein (LDL) which initiates a complex sequence of events that leads to the development of atherosclerotic plaque. Pryor, 28(1) FREE RABIC. BIOL. MED. 141-64 (2000). Vitamin E exists in at least eight naturally occurring compounds, including alpha, beta, delta and gamma tocopherol, and alpha, beta, delta and gamma tocotrienol. The tocotrienols are similar to tocopherols in molecular structure except that they contain three double bonds in the isoprenoid side chain. Dutta et al., 22(4) J. AM. COLL. NUTR. 258-68 (2003). Tocotrienols are natural analogues of tocopherols.

Tocopherols, are thought to reduce low density lipoprotein (LDL) oxidation. Id. Tocopherol supplementation therefore appears to slow down the development of atherosclerosis in coronary arteries in humans. Id.

Research suggests that tocotrienols are also beneficial against cardiovascular disease. The gamma, delta and alpha isoforms of tocotrienols are thought to decrease hepatic cholesterol production and reduce plasma cholesterol levels in subjects. Parker et al., 268(15) J. BIOL. CHEM. 11230-38 (1993).

In one embodiment, the compositions and methods of the present invention may include natural vitamin E. In a specific embodiment, the compositions and methods of the present invention may include vitamin E selected from one or more of the group consisting of alpha, beta, delta and gamma tocopherol. In another specific embodiment, the compositions and methods of the present invention may include vitamin E selected from one or more of the group consisting of alpha, beta, delta and gamma tocotrienol.

In another specific embodiment, the compositions and methods may include natural mixed tocopherols. The natural mixed tocopherols may be any combination of alpha, beta, delta and gamma tocopherol from a natural source. In another specific embodiment, the compositions and methods may include natural mixed tocotrienols. The natural mixed tocotrienols may be any combination of alpha, delta and gamma tocotrienol from a natural source.

In another specific embodiment, the compositions and methods may include the total amount of natural tocopherols in the range of about 150 IU to about 450 IU. In another specific embodiment, the compositions and methods may include natural gamma tocopherol in the range of about 90 IU to about 270 IU. In another specific embodiment, the compositions and methods may include natural gamma tocopherol in the amount of about 180 IU. In another specific embodiment, the compositions and methods may include natural delta tocopherol in the range of about 24 IU to about 72 IU. In another specific embodiment, the compositions and methods may include natural delta tocopherol in the amount of about 48 IU. In another specific embodiment, the compositions and methods may include natural alpha tocopherol in the range of about 15 IU to about 45 IU. In another specific embodiment, the compositions and methods may include natural alpha tocopherol in the amount of about 30 IU. In another specific embodiment, the compositions and methods may include natural beta tocopherol in the range of about 1.5 IU to about 4.5 IU. In another specific embodiment, the compositions and methods may include natural beta tocopherol in the amount of about 3 IU. In another specific embodiment, the compositions and methods may include the total amount of natural mixed tocotrienols in the range of about 12.5 mg to about 37.5 mg. In another specific embodiment, the compositions and methods may include the total amount of natural mixed tocotrienols in the amount of about 25 mg. In another specific embodiment, the compositions and methods may include the total amount of natural mixed tocotrienols in the form of Nutriene®. In another specific embodiment, the compositions and methods may include natural gamma tocotrienol in the range of about 0.5 mcg to about 1.7 mcg. In another specific embodiment, the compositions and methods may include natural gamma tocotrienol in the amount of about 1.1 mcg. In another specific embodiment, the compositions and methods may include natural delta tocotrienol in the range of about 62.5 mcg to about 187.5 mcg. In another specific embodiment, the compositions and methods may include natural delta tocotrienol in the amount of about 125 mcg. In another specific embodiment, the compositions and methods may include natural alpha tocotrienol in the range of about 37 mcg to about 112 mcg. In another specific embodiment, the compositions and methods may include natural alpha tocotrienol in the amount of about 75 mcg.

Omega-3 fatty acids are polyunsaturated essential fatty acids. Omega-3 fatty acids are important compounds in cardiovascular care. The benefits of increasing the intake of omega-3 fatty acids include decreased platelet adhesiveness, lowered blood pressure levels and a decreased risk of coronary artery disease. Kirs-Etherton, 106 Circulation 2747-57 (2002). Omega 3 fatty acids are common in natural sources such as fish oil. Fish oil is also believed to assist in the prevention of cardiovascular disease. von Schacky C, 2(3) Vasc. Health Risk Manag. 251-62 (2006). Two omega-3 fatty acids that are especially rich in fish oil are eicosapentaenoic acid (EPA) and docosahexaenoic acid (DHA). Studies show that EPA and DHA are particularly effective for the prevention of atherosclerosis and coronary heart disease and are therefore, the most likely reason for these beneficial features found in fish oil. Id.

In a specific embodiment, the compositions and methods of the present invention may include fish oil. In a specific embodiment, the compositions and methods of the present invention may include natural omega-3 fatty acids. In another embodiment of the present invention, the compositions and methods may include omega-3 fatty acids selected from one or more of the group consisting of eicosapentaenoic acid, docosahexaenoic acid, α-linolenic acid, stearidonic acid, eicosatetraenoic acid, docosapentaenoic acid, octadecatrienoic acid and octadecatetraenoic acid. In another specific embodiment, the compositions and methods of the present invention may include omega-3 fatty acids from fish oil. In another embodiment of the present invention, the compositions and methods may include the fish oil fatty acids eicosapentaenoic acid (EPA) and docosahexaenoic acid (DHA). In another embodiment of the present invention, the compositions and methods may include the fish oil fatty acids EPA and DHA from a natural source. In another embodiment of the present invention, the compositions and methods may comprise natural fish oil EPA omega-3 in the range of about 45 mg to about 135 mg. In another embodiment of the present invention, the compositions and methods may comprise natural fish oil EPA omega-3 in the amount of about 90 mg. In another embodiment of the present invention, the compositions and methods may comprise natural fish oil DHA omega-3 in the range of about 30 mg to about 90 mg. In another embodiment of the present invention, the compositions and methods may comprise natural fish oil DHA omega-3 in the amount of about 60 mg.

B-complex consists of eight B vitamins: vitamin $B_1$, vitamin $B_2$, vitamin $B_3$, vitamin $B_5$, vitamin $B_6$, vitamin $B_7$, vitamin $B_9$ and vitamin $B_{12}$. B vitamins are water soluble nutrients that play a role in cellular metabolism. An important role relating to cardiovascular disease is the effect of B vitamins on the reduction of homocysteine and maintaining healthy levels of particular fatty acids. It is believed that elevated levels of homocysteine may lead to increased risk of cardiovascular disease due to its numerous deleterious effects on the vascular system such as impairing endothelial function, inducing thrombosis, and increasing oxidant stress. Schlaich, 153(2) Atheroscler. 383-89 (2000); Hanratty, 85(3) Heart 326-30 (2001).

Vitamin $B_3$, or "niacin" is the common name for two compounds: nicotinic acid (also called niacin) and niacinamide (also called nicotinamide). Vitamin $B_3$ is important for maintaining healthy levels of fatty acids. For example, vitamin $B_3$ is believed to reduce low density lipoprotein (LDL) cholesterol and very low density lipoprotein (VLDL) levels and increase n high density lipoprotein (HDL) cholesterol levels.

Vitamin $B_6$, as with folate and vitamin $B_{12}$, lowers the plasma levels of homocysteine. Vitamin $B_6$ reduces the levels of homocysteine via the sulfuration pathway. Homocysteine is condensed with serine to form cystathionine, an irreversible reaction dependent on pyridoxal 5'-phosphate, the active form of vitamin $B_6$. Verhoef et al., 143(9) Am J. Epidemiol 845-59 (1996). Cystathionine is then converted to cysteine in another vitamin $B_6$-dependent reaction. Id. It is believed that through this pathway of removing plasma homocysteine, vitamin $B_6$ is an important factor in a decreased risk of cardiovascular disease.

Vitamin $B_9$, or folic acid, which is found in foods such as legumes and dark green leafy vegetables, is essential for the formation of red and white blood cells within bone marrow and plays a role in heme formation. Id at 150. Folic acid or folate, also plays an important role in carbon metabolism and the biosynthesis of purines and the pyrimidine, thymine. Folic acid also plays a role in amino acid synthesis, such as the conversion of glycine to serine and the transformation of homocysteine to methionine. It is believed that elevated levels of homocysteine may lead to increased risk of cardiovascular disease. Schlaich, 153(2) ATHEROSCLER. 383-89 (2000); Hanratty, 85(3) HEART 326-30 (2001).

Folic acid may have other physiological effects beyond its role in homocysteine breakdown that also protects against cardiovascular disease. For example, folic acid improves the levels and functioning of the health promoting, endothelial-derived compound nitric oxide (NO). Das, 19(7-8) NUTR. 686-92 (2003). Folic acid creates this effect by enhancing the activity of the enzyme nitric oxide synthase, stimulating endogenous tetrahydrobiopterin, and inhibiting generation of intracellular superoxide. These actions enhance the half-life of NO and thus create cardioprotective effects.

Vitamin $B_{12}$ can be converted to the active coenzymes, methylcobalamin and 5'-deoxyadenosylcobalamin. These coenzymes are necessary for folic acid metabolism, conversion of coenzyme A and myelin synthesis. Methylcobalamin also catalyzes the demethylation of a folate cofactor which is involved in DNA synthesis. A lack of demethylation may result in folic acid deficiency. National Research Council, RECOMMENDED DIETARY ALLOWANCES $10^{th}$ ed., 159-60 (1989). Deoxyadenosylcobalamin is the coenzyme for the conversion of methylmalonyl-CoA to succinyl-CoA, which plays a role in the citric acid cycle. Cobalamin is implicated in the proper metabolism of homocysteine, and is therefore believed to be correlated with a decreased risk of cardiovascular disease.

In another embodiment, the methods and compositions of the present invention may comprise B-complex vitamins. In a specific embodiment, the methods and compositions of the present invention may include one or more of the B vitamins selected from the group consisting of vitamin $B_1$, vitamin $B_2$, vitamin $B_3$, vitamin $B_5$, vitamin $B_6$, vitamin $B_7$, vitamin $B_9$ and vitamin $B_{12}$. In a specific embodiment, the methods and compositions of the present invention may include vitamin $B_3$ in the form of nicotinic acid. In a specific embodiment, the methods and compositions of the present invention may comprise nicotinic acid in the range of about 6.25 mg to about 18.75 mg. In a specific embodiment, the methods and compositions of the present invention may comprise nicotinic acid in the amount of about 12.5 mg.

In another specific embodiment, the methods and compositions of the present invention may include vitamin $B_3$ in the form of niacinamide ascorbate. In a specific embodiment, the methods and compositions of the present invention may comprise niacinamide ascorbate in the range of about 6.25 mg to about 18.75 mg. In a specific embodiment, the methods and compositions of the present invention may comprise niacinamide ascorbate in the amount of about 12.5 mg. In a specific embodiment, the methods and compositions of the present invention may comprise the complex niacinamide ascorbate wherein the percentage of ascorbate (vitamin C) is about 73% by weight. In a specific embodiment, the methods and compositions of the present invention may comprise the complex niacinamide ascorbate wherein the percentage of niacinamide is about 24.5% by weight.

In another specific embodiment, the methods and compositions of the present invention may comprise vitamin $B_6$ in the form of pyridoxine. In another specific embodiment, the methods and compositions of the present invention may comprise pyridoxine in the range of about 12.5 mg to about 37.5 mg. In another specific embodiment, the methods and compositions of the present invention may comprise pyridoxine in the amount of about 25 mg.

In another embodiment, the methods and compositions of the present invention may comprise vitamin $B_9$ in the form of folic acid. In a specific embodiment, the methods and compositions of the present invention may include folic acid in the range of about 0.25 mg to about 0.75 mg. In another specific embodiment, the methods and compositions of the present invention may include folic acid in the amount of about 0.5 mg.

In another specific embodiment, the methods and compositions of the present invention may comprise vitamin $B_{12}$ in the form of cyanocobalamin. In another specific embodiment, the methods and compositions of the present invention may comprise cyanocobalamin in the range of about 25 mcg to about 75 mcg. In another specific embodiment, the methods and compositions of the present invention may comprise cyanocobalamin in the amount of about 50 mcg. In another specific embodiment, the compositions and methods of the present invention may consist of nicotinic acid, niacinamide ascorbate, pyridoxine, cyanocobalamin with or without folic acid.

In a specific embodiment, the methods and compositions of the present invention may include amino acids or derivatives thereof. As used herein, an amino acid or derivative thereof refers to any amino acid, modified amino acid, natural amino acid, unnatural amino acid or amino acid analogue and the following twenty genetically encoded alpha-amino acids: alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, valine. Derivatives of amino acids may be compounds that are synthesized amino acids. Derivatives of amino acids may include peptide residues comprising from 1 to 10 amino acid residues. Amino acids or derivatives thereof may also include, but are not limited to TMG (trimethyl glycine/Betaine), L taurine, L-carnitine, acetyl-L-carnitine, N-acetylcysteine and N,N-dimethyl glycine. In another specific embodiment, the methods and compositions may include amino acids or derivatives thereof selected from one or more of the group consisting of TMG (trimethyl glycine/Betaine), L-taurine, carnitine and acetyl-L-carnitine. In another specific embodiment, the compositions and methods of the present invention may consist of TMG (trimethyl glycine/Betaine), L-taurine, carnitine and acetyl-L-carnitine.

L-carnitine is a quaternary ammonium compound that is synthesized from the amino acids lysine and methionine. L-carnitine is known to serve functions such as facilitating long chain fatty acids into mitochondria for utilization in energy generating processes. Rebouche, 6 THE FASEB JOURNAL, 3379-86 (1992). L-carnitine facilitates removal from mitochondria of short-chain and medium chain fatty acids that accumulate as a result of normal and abnormal metabolism. Id. Research points to L-carnitine also having anti-ischemic properties. L-carnitine has cardioprotective effects by acting as an antianginal agent that reduces ST segment depression and left ventricular end-diastolic pressure. Ferrari et al., 1033 ANN. N.Y. ACAD. SCI. 79-91 (2004).

In a specific embodiment, the methods and compositions of the present invention may include L-carnitine. In a specific embodiment, the methods and compositions of the present invention may include L-carnitine in the range of about 25 mg to about 75 mg. In a specific embodiment, the methods and compositions of the present invention may include L-carnitine in the amount of about 50 mg.

Acetyl-L-carnitine is the acetyl ester of L-carnitine, and as with $CoQ_{10}$, is believed to maintain optimal mitochondrial function. Acetyl-L-carnitine is also believed to improve metabolic function and decrease oxidative stress in combination with lipoic acid. Hagen et al., 99(4) PNAS 1870-75 (2002). By assisting with increasing the antioxidant status in a subject, acetyl-L-carnitine is therefore believed to have beneficial effects against the occurrence or negative effects of cardiovascular disease.

In another specific embodiment, the methods and compositions of the present invention may include acetyl-L-carnitine. In another specific embodiment, the methods and compositions of the present invention may include acetyl-L-carnitine in the range of about 6.25 mg to about 18.75 mg. In another specific embodiment, the methods and compositions of the present invention may include acetyl-L-carnitine in the amount of about 12.5 mg.

In another example, TMG (tri-methyl-glycine/Betaine) is a small N-trimethylated amino acid. Research indicates that TMG, also know as betaine, lowers plasma levels of homocysteine. Olthof et al., 133 J. NUTR. 4135-38 (2003). Specifically, TMG, a choline derivative, plays an important role in the donation of methyl groups to homocysteine to form methionine. TMG is therefore believed to assist in the prevention of cardiovascular disease by lowering plasma levels of homocysteine.

In another specific embodiment, the methods and compositions of the present invention may include TMG. In another specific embodiment, the methods and compositions of the present invention may include TMG in the range of about 25 mg to about 75 mg. In another specific embodiment, the methods and compositions of the present invention may include TMG in the amount of about 50 mg.

In another example, L-taurine (2-amino-ethanesulfonic acid) is a sulfonic amino acid which is biologically synthesized in the body of mammals. This exists in a state free from intracellular fluids, and is found in skeletal muscles, such as cerebrum, eyeball, muscles, liver and the like, free amino acid groups and at high concentrations. Taurine has been used in foods and drinks as a health additive having various functional characteristics, such as improvement of the liver function through detoxication and antioxidation actions, decreased blood cholesterol, and blood pressure adjustment. Also, it is effective in mitigating jaundice upon acute hepatitis by choleretic action, and in reducing blood neutral fat and cholesterol values in patients with hyperlipidemia.

In another specific embodiment, the methods and compositions of the present invention may include L-taurine. In another specific embodiment, the methods and compositions of the present invention may include L-taurine in the range of about 12.5 mg to about 37.5 mg. In another specific embodiment, the methods and compositions of the present invention may include L-taurine in the amount of about 25 mg.

In another specific embodiment, the methods and compositions may include antioxidants in the invention. Antioxidants may be an agent which inhibits oxidation and thus is used to prevent deterioration of preparations by the oxidative process. Specifically, antioxidants may include any substance or compound that inhibits or counteracts, either directly or indirectly, the damaging effects of oxidation in a subject. Such compounds or agents include, by way of example and without limitation, vitamin C (ascorbic acid), alpha-lipoic acid, ascorbyl palmitate, butylated hydroxyanisole, butylated hydroxytoluene, hypophosphorous acid, monothioglycerol, propyl gallate, sodium ascorbate, sodium bisulfite, sodium formaldehyde sulfoxylate, sodium metabisulfite, pycnogenol, superoxide dismutase, pine bark grape seed complex, garlic, carotenoids, choline, metabisulfite, catechin, glangin, rutin, luteolin, morin, fisetin, silymerin, ascorbyl palmitate, apigenin, gingkolides, hesperitin, cyanidin, citrin sodium bisulfite and others known to those of ordinary skill in the art.

Antioxidants may be included in the present invention for the beneficial or protective effects against heart disease. For example, vitamin C may be included in the present invention due to its preventative effects against heart disease. Vitamin C, also known as ascorbic acid, is an antioxidant commonly found in foods such as citrus fruits, potatoes, tomatoes and green vegetables. Vitamin C is a coenzyme in hydroxylation reactions, and is required for collagen synthesis, epinephrine synthesis and bile acid formation. Vitamin C has also been implemented in inhibiting atherosclerosis by being present in the extracellular fluid of the arterial wall and potentiating nitric oxide activity, thus normalizing vascular function.

In another example, the antioxidant alpha-lipoic acid may be included in the present invention. Alpha-lipoic acid plays an essential role in mitochondrial dehydrogenase reactions. Alpha-lipoic acid is believed to prevent cardiovascular disease due to its antioxidant effects. Alpha-lipoic acid has been shown to combat oxidative stress by inhibiting a variety of reactive oxidative species (ROS) and protecting against LDL oxidation. Wollin et al., 133(11) J. OF NUTR. 3327 (2003). It is through these mechanisms that alpha-lipoic acid is believed to protect against cardiovascular disease.

In another embodiment, the methods and compositions of the present invention may include antioxidants selected from one or more of the group consisting of vitamin C (ascorbic acid), alpha-lipoic acid, ascorbyl palmitate, butylated hydroxyanisole, butylated hydroxytoluene, hypophosphorous acid, monothioglycerol, propyl gallate, sodium ascorbate, sodium bisulfite, sodium formaldehyde sulfoxylate, sodium metabisulfite, pycnogenol, superoxide dismutase, pine bark grape seed complex, garlic, carotenoids, choline, metabisulfite, catechin, glangin, rutin, luteolin, morin, fisetin, silymerin, ascorbyl palmitate, apigenin, gingkolides, hesperitin, cyanidin, citrin sodium bisulfite or mixtures thereof.

In another embodiment, the methods and compositions of the present invention may include the other antioxidant, alpha-lipoic acid. In another embodiment, the methods and compositions of the present invention may include alpha-lipoic acid in the range of about 12.25 mg to about 37.5 mg. In another embodiment, the methods and compositions of the present invention may include alpha-lipoic acid in the amount of about 25 mg. In another embodiment, the methods and compositions of the present invention may include the antioxidant, vitamin C. In another embodiment, the methods and compositions of the present invention may include vitamin C in the form of calcium ascorbate. In another embodiment, the methods and compositions of the present invention may include calcium ascorbate in the range of about 125 mg to about 375 mg. In another embodiment, the methods and compositions of the present invention may include calcium ascorbate in the amount of about 250 mg.

Minerals are inorganic or non-carbon containing compounds that are essential for human nutrition and physiological processes such as nerve conduction and as structural elements in the body. Each mineral is required in certain amounts ranging from micrograms to grams per day and are found in many foods such as whole-grains. Minerals act as cofactors for numerous enzymes associated with food digestion, nucleic acid production and protein synthesis. Minerals are also thought to have a role as co-factors for antioxidant enzymes and may also reduce the risk of coronary heart disease through antithrombotic and decreased platelet-aggregating effects. Anderson et al., 70(3) AM. J. CLIN. NUTR. 307-08 (1999).

In another embodiment, the methods and compositions of the present invention may include minerals. Minerals may by in either chelated or non-chelated form, which may influence the bioavailability of the mineral. In another embodiment, the methods and compositions of the present invention may include minerals in a chelated or non-chelated form selected from one or more of the group consisting of magnesium, zinc, calcium, phosphorous, copper, manganese, chromium, selenium, sodium potassium, chloride and iron.

In another embodiment, the methods and compositions of the present invention may include minerals chelated to amino acids. In another embodiment, the methods and compositions of the present invention may include chelated minerals comprising magnesium and selenium.

Magnesium is the fourth most abundant mineral in the body and is found in foods such as green vegetables and nuts. In the body, magnesium is primarily found in bones and muscle. Magnesium is essential for the utility of many enzymes and numerous metabolic reactions in the body. Enzymes such as ATPases require the availability of magnesium in their catalytic processes. Magnesium may also play a role in coronary artery disease. Shechter et al. 102 (19) CIRCULATION 2353 (2000). Specifically, it has been demonstrated that magnesium intake in coronary artery disease patients results in the improvement of brachial artery endothelial function. Id. Magnesium is also a cofactor in myocardial ATPase enzymes that regulate the electrical activity of the heart. Magnesium is critical for the maintenance of electrochemical potentials of nerve and muscle membranes and the neuromuscular junction transmissions, particularly important in the heart. It is therefore believed that magnesium plays a beneficial role in the prevention or treatment of cardiovascular disease.

In another embodiment, the methods and compositions of the present invention may include magnesium. In a specific embodiment, the methods and compositions of the present invention may include magnesium chelated to one or more compounds. In a specific embodiment, the methods and compositions of the present invention may include magnesium in a non-chelated form. In a specific embodiment, the methods and compositions of the present invention may include magnesium chelated to an amino acid or derivative thereof. In another specific embodiment, the methods and compositions of the present inventions may include magnesium chelated to an amino acid or derivative thereof in the range of about 50 mg to about 150 mg. In another specific embodiment, the methods and compositions of the present inventions may include magnesium chelated to an amino acid or derivative thereof in the amount of about 100 mg.

The mineral selenium is an antioxidant that is fundamental to human health. Selenium is known as a catalyst for the production of active thyroid hormone. Humans also require selenium for the function of a number of selenium-dependent enzymes, called selenoproteins. Selenium is needed for the proper functioning of the immune system, and appears to be a key nutrient in counteracting the development of virulence such as HIV. Rayman, 356(9225) LANCET. 233-41 (2000). Moreover, selenium has been linked as mineral that may help prevent coronary heart disease. Wei et al., 79(1) AM. J. CLIN. NUTR., 80-5 (2004). Selenium deficiency may also play a role in causing cardiomyopathy. Lockitch et al. 52(3) AM. J. CLIN. NUTR. 572 (1990).

In a specific embodiment, the compositions and methods may include selenium. In another specific embodiment, the methods and compositions of the present invention may include selenium chelated to one or more compounds. In a specific embodiment, the methods and compositions of the present invention may include selenium in a non-chelated form. In a specific embodiment, the methods and compositions of the present invention may include selenium chelated to an amino acid or derivative thereof. In another specific embodiment, the methods and compositions of the present inventions may include a selenium-methionine chelate. In another specific embodiment, the methods and compositions of the present inventions may include the range of about 25 mcg to about 75 mcg of L-Seleno-Methionine. In another specific embodiment, the methods and compositions of the present inventions may include the amount of about 50 mcg of L-Seleno-Methionine.

Research suggests that consumption of olive oil provides a beneficial effect in regard to arterial blood pressure control. Psaltopoulou et al., 80(4) AM. J. CLIN. NUTR. 1012 (2004). Oleic acid, an omega-9 fatty acid, is the primary monounsaturated fatty acid present in olive oil. Research points to omega-9 fatty acids, specifically oleic acid, in providing the beneficial effect. 2-hydroxyoleic acid, a synthetic derivative of oleic acid, has been shown to induce substantial decreases in arterial blood pressure, mainly systolic blood pressure.

In a specific embodiment, the methods and compositions of the present invention may include other essential heart ingredients such as olive oil. Specifically, the olive oil may be extra virgin olive oil. In another specific embodiment, the methods and compositions of the present invention may include other essential heart ingredients such as omega-9 fatty acids. In another specific embodiment, the methods and compositions of the present invention may include oleic acid. In another specific embodiment, the methods and compositions of the present invention may include extra virgin olive oil in the range of about 107.5 mg to about 322.5 mg. In another specific embodiment, the methods and compositions of the present invention may include extra virgin olive oil in the amount of about 215 mg.

Lecithin, which is commonly known as a pure form of phosphatidyl choline, is a phospholipid. However, lecithin may also include phosphatidylethanolamine, and phosphatidylinositol. Lecithin helps disperse cholesterol and other lipids in body fluids so they can be removed from the body rather than from fatty plaques in the artery walls. Research suggests that lecithin promotes lower blood cholesterol levels.

In a specific embodiment, the methods and compositions of the present invention may include lecithin. In another specific embodiment, the methods and compositions of the present invention may include lecithin in the range of about 25 mg to about 75 mg. In another specific embodiment, the methods and compositions of the present invention may include lecithin in the amount of about 50 mg.

In a another embodiment, the methods and compositions of the present invention may be substantially free of other added vitamins, minerals and nutrients. The addition of other vitamins, minerals and nutrients can produce adverse side effects that can inhibit or outweigh the benefits of the compositions of the present invention. For example, vitamin D may be toxic and if the dosage is too high, can cause loss of appetite, nausea, thirst and/or stupor. Moreover, vitamin D regulates the plasma levels of calcium and phosphorus. High levels of vitamin D may enhance calcium absorption which can lead to hypercalcemia and lead to deposition of calcium in the organs, particularly the arteries. In a specific embodiment of the present invention, the compositions and methods may be substantially free of added vitamin D.

In another example, excessive intake of vitamin A induces a toxic syndrome called hyperviminosis A which may cause the liver to become cirrhotic. Moreover, pregnant women are recommended to not ingest much vitamin A because of the potential for causing congenital malformations in the developing fetus. In a specific embodiment, the compositions and methods of the present invention may be substantially free of added vitamin A.

Research suggests that various nutrients may have adverse health effects. For example, isoflavones such as genistein may have adverse side effects such as increasing the risk of cancer. Messina et al., 98(18) J. NATL. CANCER INST. 1275-84 (2006). In a specific embodiment, the compositions and methods of the present invention may be substantially free of added bioflavonoids such as genistein. In another specific embodiment, the methods and compositions of the present invention may be substantially free of another added natural biofavonoid selected from one or more of the group consisting of epicatechin, genistein, hesperidin, quercetin, rutin, narirutin, naringin, hesperetin, neohesperidin, tangeretin, nobiletin and sinensetin.

In another specific embodiment, the methods and compositions of the present invention may be substantially free of another added omega-3 fatty acid selected from one or more of the group consisting of α-linolenic acid, stearidonic acid, eicosatetraenoic acid, docosapentaenoic acid, octadecatrienoic acid and octadecatetraenoic acid.

In another specific embodiment, the methods and compositions of the present invention may be substantially free of another amino acid selected from one or more of the group consisting of proline, phenylalanine, threonine, tryptophan, histidine, isoleucine, leucine, asparagine, aspartic acid, glutamic acid, glutamine, serine, tyrosine, valine, lysine, alanine, glycine, tryptophan, cysteine, N,N-dimethyl glycine and N-acetylcysteine.

In another specific embodiment, the methods and compositions of the present invention may be substantially free of another antioxidant selected from one or more of the group consisting of ascorbyl palmitate, butylated hydroxyanisole, butylated hydroxytoluene, hypophosphorous acid, monothioglycerol, propyl gallate, sodium ascorbate, sodium bisulfite, sodium formaldehyde sulfoxylate, sodium metabisulfite, pycnogenol, superoxide dismutase, pine bark grape seed complex, garlic, carotenoids, choline, metabisulfite, catechin, glangin, rutin, luteolin, morin, fisetin, silymerin, ascorbyl palmitate, apigenin, gingkolides, hesperitin, cyanidin, citrin and sodium bisulfite.

Research suggests that increased levels of the minerals copper and/or zinc are correlated with an increased risk of gastric cancer. Lin et al., 93(10), JPN. J. CANCER RES. 1071-5 (2002). In a specific embodiment, the compositions and methods of the present invention may be free of added minerals such as zinc and/or copper. In another specific embodiment, the methods and compositions of the present invention may be substantially free of another added mineral selected from one of more of the group consisting of zinc, calcium, phosphorous, copper, manganese, chromium, sodium, potassium, chloride, and iron.

In another specific embodiment, the methods and compositions of the present invention may be administered to a patient for the prevention and/or alleviation of the occurrence or negative effects of cardiovascular disease. The prevention and/or alleviation of cardiovascular disease may include diseases or negative effects associated with the heart, arteries, or the like. Specifically, cardiovascular disease may include, but is not limited to congestive heart failure, atherosclerosis, ischemic heart disease, cardiomyopathy, hypertension, coronary artery disease, high blood pressure, elevated cholesterol, elevated C-Reactive protein, elevated Lipoprotein A, elevated homocysteine, elevated fibrinogen, arrhythmia, hypercoaguable states, endocarditis and thrombogenicity.

A specific embodiment of the present invention may comprise compositions in the dosage form of a soft-gel. A soft-gel is a one-piece, sealed, soft gelatin shell that contains a solution, a suspension, or a semi-solid paste. Soft-gels are predominantly used to contain liquids wherein the active ingredients are present in the dissolved or suspended state. Soft-gels have been widely known and used for many years and for a variety of purposes. Because soft-gels have properties that are quite different from two-piece, hard shell capsules, the soft-gels are capable of retaining a liquid fill material. Soft-gels are often used to encapsulate consumable materials, including vitamins, dietary supplements, pharmaceuticals, and the like, in a liquid vehicle or carrier. Soft-gels are a unique dosage form that can provide distinct advantages over more traditional dosage forms such as tablets, hard-shell capsules, and liquids. These advantages include patient compliance and consumer preference, improved bioavailability, speed of product development in many cases, shortened manufacturing time, enhanced drug stability due to less exposure of the active ingredient to oxygen, excellent dose uniformity, and product differentiation.

A specific embodiment of the present invention may comprise swallowable compositions. Swallowable compositions are well known in the art and are those that do not readily dissolve when placed in the mouth and may be swallowed whole without any chewing or discomfort. In a specific embodiment of the present invention the swallowable compositions may have a shape containing no sharp edges and a smooth, uniform and substantially bubble free outer coating.

To prepare the swallowable compositions of the present invention, each of the active ingredients may be combined in intimate admixture with a suitable carrier according to conventional compounding techniques. In a specific embodiment of the swallowable compositions of the present invention, the surface of the compositions may be coated with a polymeric film. Such a film coating has several beneficial effects. First, it reduces the adhesion of the compositions to the inner surface of the mouth, thereby increasing the patient's ability to swallow the compositions. Second, the film may aid in masking the unpleasant taste of certain drugs. Third, the film coating may protect the compositions of the present invention from atmospheric degradation. Polymeric films that may be used in preparing the swallowable compositions of the present invention include vinyl polymers such as polyvinyl pyrrolidone, polyvinyl alcohol and acetate, cellulosics such as methyl and ethyl cellulose, hydroxyethyl cellulose and hydroxylpropyl methylcellulose, acrylates and methacrylates, copolymers such as the vinyl-maleic acid and styrene-maleic acid types, and natural gums and resins such as zein, gelatin, shellac and acacia. Pharmaceutical carriers and formulations for swallowable compounds are well known to those of ordinary skill in the art. See generally, e.g., WADE & WALLER, HANDBOOK OF PHARMACEUTICAL EXCIPIENTS ($2^{nd}$ ed. 1994).

In a specific embodiment of the present invention, the compositions may comprise chewable compositions. Chewable compositions are those that have a palatable taste and mouthfeel, are relatively soft and quickly break into smaller pieces and begin to dissolve after chewing such that they are swallowed substantially as a solution.

In order to create chewable compositions, certain ingredients should be included to achieve the attributes just described. For example, chewable compositions should include ingredients that create pleasant flavor and mouthfeel and promote relative softness and dissolvability in the mouth. The following discussion describes ingredients that may help to achieve these characteristics.

Chewable compositions preferably have a pleasant or palatable flavor. Palatable flavors may be achieved by including sweetening agents and/or flavorants. Sweetening agents that may be included in the compositions of the present invention include, by way of example and without limitation, sucrose, fructose, high fructose corn syrup, dextrose, saccharin sodium, maltodextrin, aspartame, potassium acesulfame, neohesperidin dihydrochalcone, sucralose, monoammonium glycyrrhizinate, and others known to those of ordinary skill in the art. As used herein, the term "flavorant" means natural or artificial compounds used to impart a pleasant flavor and often odor to a pharmaceutical preparation. Flavorants that may be used in the present invention include, for example and without limitation, natural and synthetic flavor oils, flavoring aromatics, extracts from plants, leaves, flowers, and fruits and combinations thereof. Such flavorants include, by way of example and without limitation, anise oil, cinnamon oil, vanilla, vanillin, cocoa, chocolate, natural chocolate flavor, menthol, grape, peppermint oil, oil of wintergreen, clove oil, bay oil, anise oil, eucalyptus, thyme oil, cedar leave oil, oil of nutmeg, oil of sage, oil of bitter almonds, cassia oil; citrus oils, such as lemon, orange, lime and grapefruit oils; and fruit essences, including apple, pear, peach, berry, wildberry, date, blueberry, kiwi, strawberry, raspberry, cherry, plum, pineapple, and apricot. All of these flavorants are commercially available. In a specific embodiment of the present invention, flavorants that may be used include natural berry extracts and natural mixed berry flavor, as well as citric and malic acid. The amount of flavorants used may depend on a number of factors, including desired taste characteristics. While not necessary, one or more of these sweetening agents and/or flavorants also may be included in the swallowable compositions of the present invention.

In addition to having a palatable flavor, chewable compositions also should have a pleasant mouthfeel. A variety of ingredients can be included in the compositions of the present invention to enhance mouthfeel.

In the chewable compositions of the present invention, sugars such as white sugar, corn syrup, sorbitol (solution), maltitol (syrup), oligosaccharide, isomaltooligosaccharide, sucrose, fructose, lactose, glucose, lycasin, xylitol, lactitol, erythritol, mannitol, isomaltose, dextrose, polydextrose, dextrin, compressible cellulose, compressible honey, compressible molasses and mixtures thereof may be added to improve mouthfeel and palatability. Further, by way of example and without limitation, fondant or gums such as gelatin, agar, arabic gum, guar gum, and carrageenan may be added to improve the chewiness of the compositions. Fatty materials that may be included in the present invention include, by way of example and without limitation, vegetable oils (including palm oil, palm hydrogenated oil, corn germ hydrogenated oil, castor hydrogenated oil, cotton-seed oil, olive oil, peanut oil, palm olein oil, and palm stearin oil), animal oils (including refined oil and refined lard whose melting point ranges from 30° to 42° C.), Cacao fat, margarine, butter, and shortening.

Alkyl polysiloxanes (commercially available polymers sold in a variety of molecular weight ranges and with a variety of different substitution patterns) also may be used in the present invention to enhance the texture, the mouthfeel, or both of the chewable nutritional supplement compositions described herein. By "enhance the texture" it is meant that the alkyl polysiloxane improves one or more of the stiffness, the brittleness, and the chewiness of the chewable supplement, relative to the same preparation lacking the alkyl polysiloxane. By "enhance the mouthfeel" it is meant that the alkyl polysiloxane reduces the gritty texture of the supplement once it has liquefied in the mouth, relative to the same preparation lacking the alkyl polysiloxane.

Alkyl polysiloxanes generally comprise a silicon and oxygen-containing polymeric backbone with one or more alkyl groups pending from the silicon atoms of the back bone. Depending upon their grade, they can further comprise silica gel. Alkyl polysiloxanes are generally viscous oils. Exemplary alkyl polysiloxanes that can be used in the swallowable, chewable or dissolvable compositions of the present invention include, by way of example and without limitation, monoalkyl or dialkyl polysiloxanes, wherein the alkyl group is independently selected at each occurrence from a $C_1$-$C_6$-alkyl group optionally substituted with a phenyl group. A specific alkyl polysiloxane that may be used is dimethyl polysiloxane (generally referred to as simethicone). More specifically, a granular simethicone preparation designated simethicone GS may be used. Simethicone GS is a preparation which contains 30% simethicone USP. Simethicone USP contains not less than about 90.5% by weight $(CH_3)_3$—$Si\{OSi(CH_3)_2\}CH_3$ in admixture with about 4.0% to about 7.0% by weight $SiO_2$.

To prevent the stickiness that can appear in conventional chewable compositions and to facilitate conversion of the active ingredients to emulsion or suspension upon taking, the compositions of the present invention, may further comprise emulsifiers such as, by way of example and without limitation, glycerin fatty acid ester, sorbitan monostearate, sucrose fatty acid ester, lecithin and mixtures thereof. In a specific embodiment, one or more of such emulsifiers may be present in an amount of about 0.01% to about 5.0%, by weight of the administered compositions. If the level of emulsifier is lower or higher than the said range, the emulsification cannot be realized, or wax value will rise.

Chewable compositions should begin to break and dissolve in the mouth shortly after chewing begins such that the compositions can be swallowed substantially as a solution. The dissolution profile of chewable compositions may be enhanced by including rapidly water-soluble fillers and excipients. Rapidly water-soluble fillers and excipients preferably dissolve within about 60 seconds of being wetted with saliva. Indeed, it is contemplated that if enough water-soluble excipients are included in the compositions of the present invention, they may become dissolvable rather than chewable composition forms. Examples of rapidly water soluble fillers suitable for use with the present invention include, by way of example and without limitation, saccharides, amino acids and the like. In a specific embodiment, the saccharide may be a mono-, di- or oligosaccharide. Examples of saccharides which may be added to the compositions of the present invention include, by way of example and without limitation, sorbitol, glucose, dextrose, fructose, maltose and xylitol (all monosaccharides); and sucrose, lactose, glucose, galactose and mannitol (all disaccharides). Other suitable saccharides are oligosaccharides. Examples of oligosaccharides are dextrates and maltodextrins. Other water soluble excipients that may be used with the present invention include, by way of example and without limitation, amino acids such as alanine, arginine, aspartic acid, asparagine, cysteine, glutamic acid, glutamine, glycine, histidine, isoleucine, leucine, lysine, methionine, phenylalanine, proline, serine, threonine, tryptophan, tyrosine and valine.

Disintegrants also may be included in the compositions of the present invention in order to facilitate dissolution. Disentegrants, including permeabilising and wicking agents, are capable of drawing water or saliva up into the compositions which promotes dissolution from the inside as well as the outside of the compositions. Such disintegrants, permeabilising and/or wicking agents that may be used in the present invention include, by way of example and without limitation, starches, such as corn starch, potato starch, pre-gelatinized and modified starches thereof, cellulosic agents, such as Ac-di-sol, montmorrilonite clays, cross-linked PVP, sweeteners, bentonite, microcrystalline cellulose, croscarmellose sodium, alginates, sodium starch glycolate, gums, such as agar, guar, locust bean, karaya, pectin, Arabic, xanthan and tragacanth, silica with a high affinity for aqueous solvents, such as colloidal silica, precipitated silica, maltodextrins, beta-cyclodextrins, polymers, such as carbopol, and cellulosic agents, such as hydroxymethylcellulose, hydroxypropylcellulose and hydroxyopropylmethylcellulose.

Finally, dissolution of the compositions may be facilitated by including relatively small particles sizes of the ingredients used.

In addition to those described above, any appropriate fillers and excipients may be utilized in preparing the swallowable, chewable and/or dissolvable compositions of the present invention so long as they are consistent with the objectives described herein. For example, binders are substances used to cause adhesion of powder particles in granulations. Such compounds appropriate for use in the present invention include, by way of example and without limitation, acacia, compressible sugar, gelatin, sucrose and its derivatives, maltodextrin, cellulosic polymers, such as ethylcellulose, hydroxypropylcellulose, hydroxypropylmethyl cellulose, carboxymethylcellulose sodium and methylcellulose, acrylic polymers, such as insoluble acrylate ammoniomethacrylate copolymer, polyacrylate or polymethacrylic copolymer, povidones, copovidones, polyvinylalcohols, alginic acid, sodium alginate, starch, pregelatinized starch, guar gum, polyethylene glycol and others known to those of ordinary skill in the art.

Diluents also may be included in the compositions of the present invention in order to enhance the granulation of the compositions. Diluents can include, by way of example and without limitation, microcrystalline cellulose, sucrose, dicalcium phosphate, starches, lactose and polyols of less than 13 carbon atoms, such as mannitol, xylitol, sorbitol, maltitol and pharmaceutically acceptable amino acids, such as glycin, and their mixtures.

Lubricants are substances used in composition formulations that reduce friction during composition compression. Lubricants that may be used in the present invention include, by way of example and without limitation, stearic acid, calcium stearate, magnesium stearate, zinc stearate, talc, mineral and vegetable oils, benzoic acid, poly(ethylene glycol), glyceryl behenate, stearyl fumarate, and others known to those of ordinary skill in the art.

Glidants improve the flow of powder blends during manufacturing and minimize composition weight variation. Glidants that may be used in the present invention include, by way of example and without limitation, silicon dioxide, colloidal or fumed silica, magnesium stearate, calcium stearate, stearic acid, cornstarch, talc and others known to those of ordinary skill in the art.

Colorants also may be included in the nutritional supplement compositions of the present invention. As used herein, the term "colorant" includes compounds used to impart color to pharmaceutical preparations. Such compounds include, by way of example and without limitation, FD&C Red No. 3, FD&C Red No. 20, FD&C Yellow No. 6, FD&C Blue No. 2, D&C Green No. 5, FD&C Orange No. 5, D&C Red No. 8, caramel, and ferric oxide, red and others known to those of ordinary skill in the art. Coloring agents also can include pigments, dyes, tints, titanium dioxide, natural coloring agents, such as grape skin extract, beet red powder, beta carotene, annato, carmine, turmeric, paprika and others known to those of ordinary skill in the art. It is recognized that no colorant is required in the nutritional supplement compositions described herein.

If desired, the compositions of the present invention may be sugar coated or enteric coated by standard techniques. The unit dose forms may be individually wrapped, packaged as multiple units on paper strips or in vials of any size, without limitation. The swallowable, chewable or dissolvable compositions of the present invention may be packaged in unit dose, rolls, bulk bottles, blister packs and combinations thereof, without limitation.

The swallowable, chewable or dissolvable compositions of the present invention may be prepared using conventional methods and materials known in the pharmaceutical art. For example, U.S. Pat. Nos. 5,215,754 and 4,374,082 relate to methods for preparing swallowable compositions. U.S. Pat. No. 6,495,177 relates to methods to prepare chewable nutritional supplements with improved mouthfeel. U.S. Pat. No. 5,965,162, relates to compositions and methods for preparing multi-vitamin comestible units which disintegrate quickly in the mouth, especially when chewed. Further, all pharmaceutical carriers and formulations described herein are well known to those of ordinary skill in the art, and determination of workable proportions in any particular instance will generally be within the capability of the person skilled in the art. Details concerning any of the excipients of the invention may be found in WADE & WALLER, HANDBOOK OF PHARMACEUTICAL EXCIPIENTS (2nd ed. 1994). All active ingredients, fillers and excipients are commercially available from companies such as Aldrich Chemical Co., FMC Corp, Bayer, BASF, Alexi Fres, Witco, Mallinckrodt, Rhodia, ISP, and others.

Other objectives, features and advantages of the present invention will become apparent from the following specific examples. The specific examples, while indicating specific embodiments of the invention, are provided by way of illustration only. Accordingly, the present invention also includes those various changes and modifications within the spirit and scope of the invention that may become apparent to those skilled in the art from this detailed description. The invention will be further illustrated by the following non-limiting examples.

Without further elaboration, it is believed that one skilled in the art, using the preceding description, can utilize the present invention to the fullest extent. The following examples are illustrative only, and not limiting of the remainder of the disclosure in any way whatsoever.

Example 1

A composition of the following formulation was prepared in a softgel form by standard methods known to those skilled in the art:

| | |
|---|---|
| Natural $CoQ_{10}$ | 30 mg |
| Natural grape seed extract (OPC) | 50 mg |
| Natural Mixed Tocopherols (total) | 300 IU |
| d-gamma tocopherol | 180 IU |
| d-delta tocopherol | 48 IU |
| d-alpha tocopherol | 30 IU |
| d-beta tocopherol | 3 IU |
| Natural Mixed Tocotrienols (total) | 25 mg |

-continued

| | |
|---|---|
| gamma-tocotrienol | 1.100 mcg |
| delta-tocotrienol | 125 mcg |
| alpha-tocotrienol | 75 mcg |
| Vitamin C (as calcium ascorbate, 80% Vitamin C) | 250 mg |
| Natural fish oil EPA Omega-3 | 90 mg |
| Natural fish oil DHA Omega-3 | 60 mg |
| Alpha-lipoic acid | 25 mg |
| Folic acid | 0.5 mg |
| Vitamin $B_3$ (niacinamide ascorbate, 73% as vitamin C) | 12.5 mg |
| Vitamin $B_3$ (nicotinic acid) | 12.5 mg |
| Vitamin $B_6$ (pyridoxine hydrochloride) | 25 mg |
| Vitamin $B_{12}$ (cyanocobalamin) | 50 mcg |
| Magnesium (amino acid chelate) | 100 mg |
| L-Seleno-Methionine (amino acid chelate) | 50 mcg |
| Acetyl-L-Carnitine | 12.5 mg |
| L-Carnitine | 50 mg |
| TMG (Tri-Methyl-Glycine/Betaine) | 50 mg |
| L-Taurine | 25 mg |

Other Nutrients:

| | |
|---|---|
| Extra Virgin Olive Oil | 215 mg |
| Lecithin | 50 mg |

Example 2

A study is undertaken to evaluate the effectiveness of the compositions of the present invention in the treatment of patients. The objective of the study is to determine whether oral intake of the compositions results in an improvement of the nutritional status of patients with regard to the specific vitamins and nutrients contained in the administered compositions.

A double-blind, placebo controlled study is conducted over a six-month period. A total of 120 subjects, aged 30-45 years, are chosen for the study. An initial assessment of the nutritional status of each subject is conducted and detected by methods known to those of ordinary skill in the art. For example, $CoQ_{10}$ is measured column-switching high performance liquid chromatography (HPLC) using a reverse-phase analytical column with uv detection at 275 nm. Omega-3 and Omega-9 fatty acids are measured and quantified using gas chromatography procedures. Vitamin $B_6$ is measured using high performance liquid chromatography (HPLC). Erythrocyte transketolase activity is used to measure vitamin $B_1$ levels. Vitamin $B_3$ levels are assessed by measuring urinary excretion of N' methylnicotinamide and its pyridone. Folic Acid is measured by radioimmunoassay (RIA), specifically The Solid Phase No Biol Folic Acid Kit (Diagnostic Products, Los Angeles, Calif.). Vitamin $B_{12}$ is measured by RIA using human intrinsic factor as a binder. Vitamin C levels are measured by spectrophotometric and colorimetric methods. The peroxide hemolysis test is used to determine vitamin E status. Magnesium levels are measured by absorbance of a magnesium chelate with xylidl blue at 660 nM. Alpha lipoic acid is measureing using HPLC with electrochemical detection. OPC's are measured using Maldi Tof mass spectrometry. Selenium is measured fluorometrically. Amino acids or derivatives thereof are detected by electrospray tandem mass spectrometry.

The 120 subjects are separated into four groups of 30. In a first group comprising men and in a second group comprising women, each subject is administered one dosage form of the composition as described in Example 1 once a day. In a third group comprising men and a fourth group comprising women, each subject is administered one placebo dosage form once a day. Thus, dosage form administration occurs every 24 hours. No other nutritional supplements are taken by the subjects during the assessment period.

An assessment of the nutritional status of each subject is conducted utilizing the methods described above at one month intervals for a six month period. The data is evaluated using multiple linear regression analysis and a standard t-test. In each analysis, the baseline value of the outcome variable is included in the model as a covariant. Treatment by covariant interaction effects is tested by the method outlined by Weigel & Narvaez, 12 CONTROLLED CLINICAL TRIALS 378-94 (1991). If there are no significant interaction effects, the interaction terms are removed from the model. The regression model assumptions of normality and homogeneity of variance of residuals are evaluated by inspection of the plots of residuals versus predicted values. Detection of the temporal onset of effects is done sequentially by testing for the presence of significant treatment effects at 1, 2, 3, 4, 5, and 6 months, proceeding to the earlier time in sequence only when significant effects have been identified at each later time period. Changes from the baseline within each group are evaluated using paired t-tests. In addition, analysis of variance is performed on all baseline measurements and measurable subject characteristics to assess homogeneity between groups. All statistical procedures are conducted using the Statistical Analysis System (SAS Institute Inc., Cary, N.C.). An alpha level of 0.05 is used in all statistical tests.

A statistically significant improvement in the nutritional status of all vitamin and nutrient levels measured is observed in the treated subjects over the controls upon completion of the study. Therefore, the study confirms that oral administration of the compositions of the present invention is effective in improving the nutritional status of patients.

While specific embodiments of the present invention have been described, other and further modifications and changes may be made without departing from the spirit of the invention. All further and other modifications and changes are included that come within the scope of the invention as set forth in the claims. The disclosure of all publications cited above are expressly incorporated by reference in their entireties to the same extent as if each were incorporated by reference individually.

What is claimed is:

1. A composition for alleviating a patient from the negative effects of cardiovascular disease consisting essentially of: therapeutically effective amounts of lecithin, extra virgin olive oil, L-taurine, trimethyl glycine/Betaine, L-carnitine, acetyl-L-carnitine, L-Seleno-Methionine, magnesium chelated to an amino acid, vitamin B-12, vitamin B-6, vitamin B-3, folate, DHA omega-3, EPA omega-3, vitamin C, alpha lipoic acid, grape seed extract, mixed tocotrienols, mixed tocopherols, and CoQ10, wherein said composition is in a form selected from the group consisting of pills, capsules, tablets, gel caplets, softgels, lozenges, and wafers.

* * * * *